(12) United States Patent
Han

(10) Patent No.: US 10,485,634 B2
(45) Date of Patent: Nov. 26, 2019

(54) PALATE ANCHORAGE DEVICE FOR ORTHODONTICS

(71) Applicant: Byeong-Ju Han, Daejeon (KR)

(72) Inventor: Byeong-Ju Han, Daejeon (KR)

(73) Assignee: Byeong-Ju Han, Daejeon (KR)

( * ) Notice: Subject to any disclaimer, the term of this patent is extended or adjusted under 35 U.S.C. 154(b) by 0 days.

(21) Appl. No.: 15/759,708

(22) PCT Filed: Aug. 9, 2016

(86) PCT No.: PCT/KR2016/008729
§ 371 (c)(1),
(2) Date: Mar. 13, 2018

(87) PCT Pub. No.: WO2017/052069
PCT Pub. Date: Mar. 30, 2017

(65) Prior Publication Data
US 2019/0046292 A1    Feb. 14, 2019

(30) Foreign Application Priority Data

Sep. 22, 2015  (KR) .......................... 10-2015-0133470

(51) Int. Cl.
A61C 7/02 (2006.01)
A61C 8/00 (2006.01)
A61C 7/14 (2006.01)

(52) U.S. Cl.
CPC ................ *A61C 7/02* (2013.01); *A61C 7/146* (2013.01); *A61C 8/0096* (2013.01)

(58) Field of Classification Search
CPC .... A61C 7/02; A61C 7/10; A61C 7/14; A61C 7/146; A61C 7/00; A61C 8/0096;
(Continued)

(56) References Cited

U.S. PATENT DOCUMENTS 4,988,351 A   1/1991  Paulos et al.
6,048,204 A *  4/2000  Klardie ................ A61C 8/0022
                                                433/174
(Continued)

FOREIGN PATENT DOCUMENTS

JP     2008-17930 A       1/2008
KR    20-2012-0001388     2/2012
(Continued)

OTHER PUBLICATIONS

Translation of WO 2016/016474 retrieved from https://patentscope.wipo.int/search/en/detail.jsf?docId=WO2016016474&tab=PCTDESCRIPTION&maxRec=1000 (Year: 2019).*

*Primary Examiner* — Heidi M Eide
(74) *Attorney, Agent, or Firm* — Lewis Roca Rothgerber Christie LLP

(57) ABSTRACT

The present invention relates to a palatal anchor plate, which is fixedly installed to mid-palatal area (the roof of a mouth) and provides a rigid orthodontic anchorage for tooth movement, whereby the palatal anchor plate reduces a counteraction (movement of a tooth that is used as an anchorage), which occurs when a tooth is used as an orthodontic anchorage, and provides a rigid orthodontic anchorage for tooth movement in various directions, which is difficult to obtain when a tooth is used as an orthodontic anchorage.

5 Claims, 3 Drawing Sheets

(58) Field of Classification Search
CPC ........... A61C 8/0031; A61C 7/80; A61C 7/06;
A61C 7/303; A61C 7/08
See application file for complete search history.

(56) References Cited

U.S. PATENT DOCUMENTS

| | | | |
|---|---|---|---|
| 2007/0259306 A1 | 11/2007 | Raines, Jr. et al. | |
| 2013/0122446 A1* | 5/2013 | Lee ........................ | A61C 7/00 433/8 |
| 2013/0189640 A1* | 7/2013 | Kook ................... | A61C 8/0031 433/18 |
| 2015/0313659 A1* | 11/2015 | Miyawaki ................ | A61C 7/00 606/303 |

FOREIGN PATENT DOCUMENTS

| | | | | |
|---|---|---|---|---|
| WO | WO 2014/088116 A1 | 6/2014 | | |
| WO | WO 2016/016474 | * | 2/2016 | ............. A61B 17/70 |

\* cited by examiner

Conventional Art

[Fig. 2]
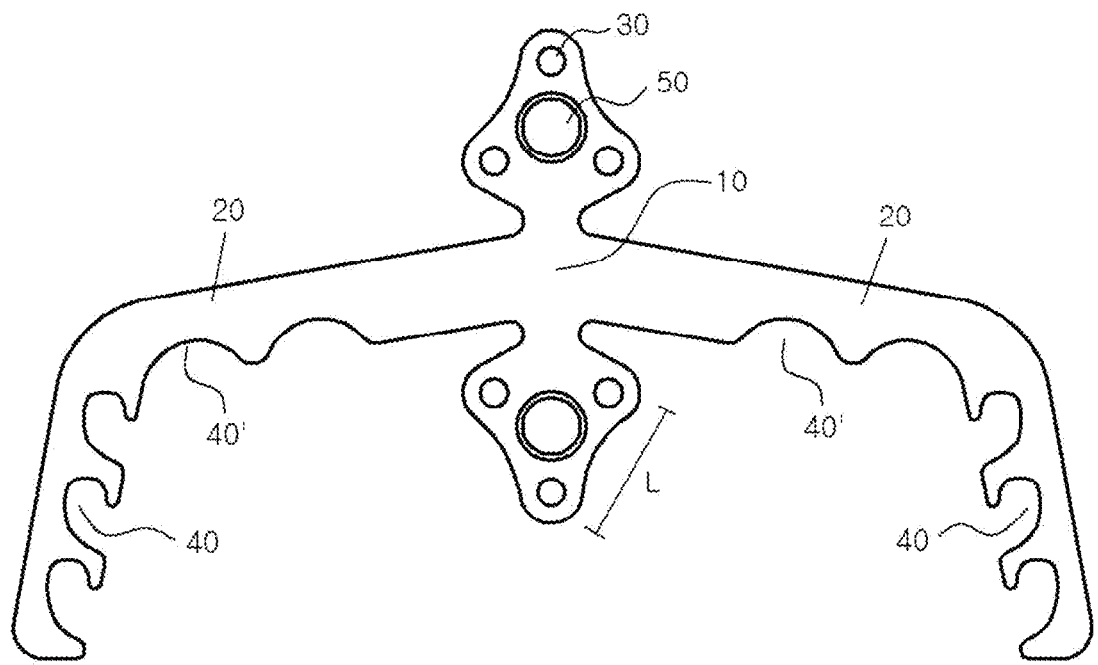
[Fig. 3]
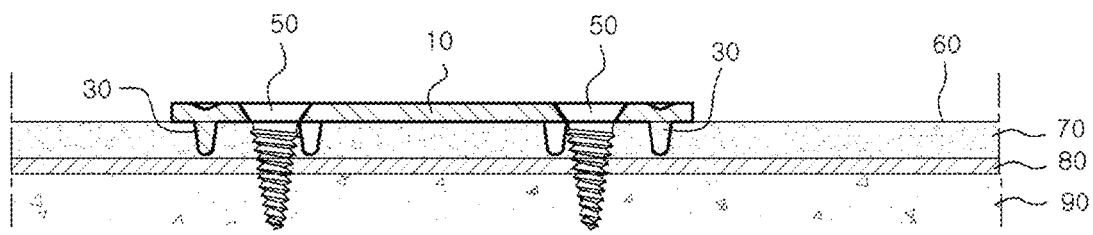

[Fig. 4]
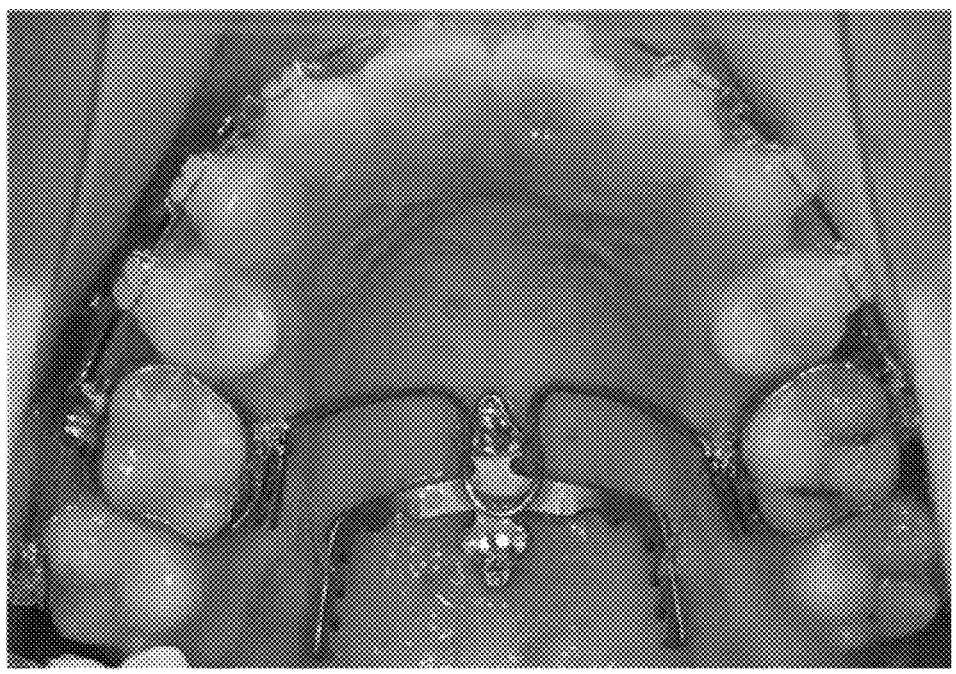

PALATE ANCHORAGE DEVICE FOR ORTHODONTICS

CROSS-REFERENCE TO RELATED APPLICATION(S)

This application is a National Phase Patent Application and claims priority to and the benefit of International Application Number PCT/KR2016/008729, filed on Aug. 9, 2016, which claims priority to Korean Patent Application Number 10-2015-0133470, filed on Sep. 22, 2015, the entire contents of all of which are incorporated herein by reference.

TECHNICAL FIELD

The present invention relates to a palatal anchor plate, which is fixedly installed to mid-palatal area (the roof of a mouth) and provides a rigid orthodontic anchorage for tooth movement, whereby the palatal anchor plate reduces a counteraction (movement of a tooth that is used as an anchorage), which occurs when a tooth is used as an orthodontic anchorage, and provides a rigid orthodontic anchorage for tooth movement in various directions, which is difficult to obtain when a tooth is used as an orthodontic anchorage.

BACKGROUND ART

In order to treat improper positioning of teeth and skeletal disharmony of the face, typically brackets are attached to the teeth and connected to each other by an orthodontic steel wire to apply continuous force to the teeth in the desired direction to cause movement of the teeth and to improve skeletal disharmony. However, when attempts are made to move the teeth, counteraction occurs according to the law of force (counteraction meaning movement of a tooth or teeth that serve as an orthodontic anchorage for moving another tooth or teeth). Therefore, various methods for reducing the counteraction have been devised and used. However, there is still a demand for counter reaction methods that are easier and less invasive procedures to patients.

As such an attempt, an anchoring plate is installed to the palate (palate; roof of mouth that separates the oral cavity and the nasal cavity from each other), brackets or similar devices are attached to the teeth to be moved, and a spring or a rubber band (power chains or power threads) are connected between the anchor plate and the brackets to apply the tension to the teeth. In this case, in order to install the anchor plate to the palate, a method of fixing the anchor plate in the oral cavity by implanting screws (screws) into the palatal bone is used. However, due to the presence of the soft tissue and no proper stops not to impinge the soft tissues between a palatal anchor plate and the palatal bone, necrosis of the mucous membranes of the palate and inflammation around the screw and anchor plate occurs frequently. Such inflammation not only causes pain and discomfort to the patient, but also leads to dislodgement of screws, which is highly likely to result in dislocation of the palatal anchor plate.

As a method for solving this problem, there is a method of exposing the cortical bone through a flap operation, then fixing an anchor plate to a palate with screws, and finally suturing the incision with a medical suture. However, this method is difficult to perform due to the complexity of the procedure and the rigid structure of palatal mucosa. Furthermore, since this procedure is an invasive procedure requiring incision of the mucous membrane, it is considered a treatment that increases the burden to the patient.

In the Korea Utility Model No. 20-0464089 (Dec. 4, 2012), although the convenience of the procedure has been improved by directly fixing a palatal anchor plate to the mucous membrane with screws without incision the mucosa membrane, it is difficult to avoid necrosis and inflammation attributable to compression of the tissue by an anchor plate at a contact portion of the palatal mucous membrane.

Therefore, to solve the above problems, there is an urgent need to develop new technology that goes beyond typical orthodontic treatments that uses a tooth as an orthodontic anchorage, by changing the design of a palatal anchor plate, whereby enabling ease of the procedure and enhancing convenience for patients.

DISCLOSURE

Technical Problem

The present invention has been made to solve the above-mentioned problems, and relates to a palatal anchor plate that is fixedly installed to the mid-palatal area (the roof of a mouth) to secure rigid orthodontic anchorage for tooth movement and for modification of the skeletal structure. An objective of the present invention is to provide a palatal anchor plate being capable of minimizing inflammation of palatal tissues, thereby providing a stable and rigid orthodontic anchorage during a long-term orthodontic treatment period by allowing force to be applied in various directions required for movement of teeth and modification of the skeletal structure.

Technical Solution

In order to achieve the above objective, the present invention provides a palatal anchor plate comprising: a base member (10) fixable to a palate by screws during orthodontic treatment of a tooth; and a hook portion (20) symmetrically extending leftward and rightward from the base member (10), wherein, the base member (10) has screw holes at a front portion and a rear portion thereof respectively, and around each of the screw holes (50), three cylindrical protrusions (30) are formed on a palatal side and arranged in a tripod shape, engagement recesses (40) and (40') are positioned a predetermined distance from each other and formed at a posterior edge of each of a left portion and a right portion of the hook portion (20), thereby enabling engagement between the hook portion and a traction member, and the palatal anchor plate is made of pure titanium ASTM F67 Grade 3.

Means for solving the other specific problems according to the present invention is described in the following detailed description section of the present disclosure.

Advantageous Effects

According to the present invention, it is possible to minimize inflammation of the soft tissue of the palate by minimizing a contact area. And it enables to keep distance between anchor plate and palatal mucosa by bi-tripod protrusions on the palatal side of the anchor plate and not to impinge the palatal mucosa. In addition, since the material of the palatal anchor plate is pure titanium ASTM F67 Grade 3, the palatal anchor plate has an advantage that it can be easily adjusted so as to conform to the contour of the palate of an individual patient.

Furthermore, since the hook portion is provided with a plurality of engagement recesses to be engaged with traction wires connected to traction members to fasten the traction members to an anchorage, traction forces can be applied to the teeth in various directions. Since traction forces can be applied in various directions, the palatal anchor plate can be not only used for incisor retraction but also can be used as an anchor for molar retraction and intrusion, which can be difficult to obtain when teeth are used as anchors.

DESCRIPTION OF DRAWINGS

FIG. 2 is a view illustrating the overall construction of the palatal anchor plate according to the present invention;

FIG. 3 is a cross-sectional view illustrating a state in which a base member and a protrusion of the palatal anchor plate according to the present invention are fixed to the cortical bone of a palate; and FIG. 4 is a photograph showing a state in which the palatal anchor plate according to the present invention is installed to the palate.

BEST MODE INVENTION

Figure 1:
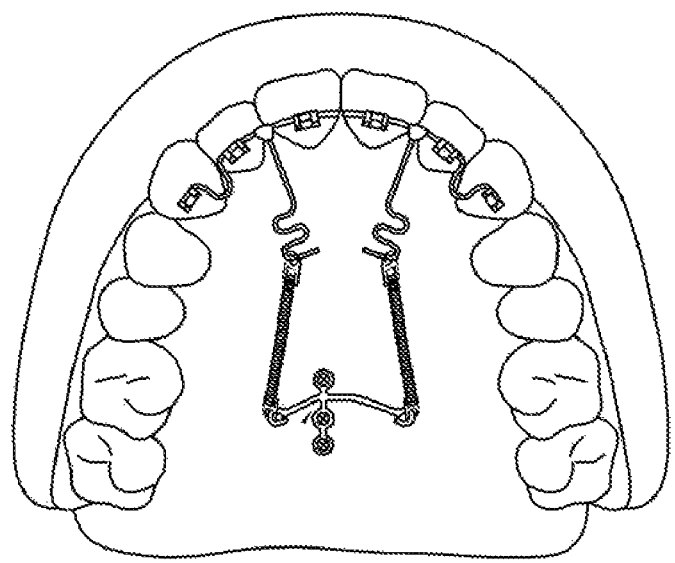
FIG. 1 is a view illustrating a state in which a palatal anchorage according to a conventional art is installed in an oral cavity.

Hereinafter, embodiments of the present invention will be described in detail with reference to the accompanying drawings. The embodiments of the present invention are provided to convey through and complete description of the present invention to those ordinarily skilled in the art. Therefore, the shapes of elements in the drawings are simplified for clarity.

First, the palatal anchor plate for orthodontic treatment according to the present invention comprises a base member (10) fixable to a palate by screws during orthodontic treatment of a tooth; and a hook portion (20) symmetrically extending leftward and rightward from the base member (10), wherein, the base member (10) has screw holes at a front portion and a rear portion thereof respectively, and around each of the screw holes (50), three cylindrical protrusions (30) are formed on a palatal side and arranged in a tripod shape, engagement recesses (40) and (40') are positioned a predetermined distance from each other and formed at a posterior edge of each of a left portion and a right portion of the hook portion (20), thereby enabling engagement between the hook portion and a traction member, and the palatal anchor plate is made of pure titanium ASTM F67 Grade 3.

As illustrated in FIG. 2, the palatal anchor plate is composed of the base member (10), the hook portion (20) including a left portion and a right portion which are in a pair, and the protrusion (30) composed of cylindrical protrusions among which three are arranged in a tripod shape at the front portion of the base member (10) and the other three are arranged in an inverted form at the rear portion of the base member (10).

As illustrated in FIGS. 2 and 3, the base member (10) among the elements of the present invention is located at the center of the palatal anchor plate for orthodontic treatment. Screws (not denoted by reference symbol numbers) are driven into the palate through the respective holes (50) formed at the front portion and the rear portion of the base member (10), so that the palatal anchor plate for orthodontic treatment fixedly installed to the palate.

Meanwhile, according to a conventional art, as illustrated in FIG. 1, a conventional palatal anchor plate is fixed to the palate of a patient by screws into the palate through multiple holes formed at a front portion and a rear portion of the palatal anchor plate. In this case, the palatal tissue around the palatal anchor plate and screws is compressed, which is likely to lead to necrosis of the palatal tissue and the increase of the granulation tissue due to the subsequent inflammation, thereby resulting in a high possibility of dislodgement of the screws and eventually resulting dislocation of the palatal anchor plate from the palate.

The inventors of the present disclosure have conceived and completed the present invention as a result of long-term intensive research into a solution to the problems described above. The inventors of the present disclosure have found that, as shown in FIG. 2, the solution is the protrusion (30) composed of cylindrical protrusions arranged around the screw holes (50). Among the cylindrical protrusions, three are symmetrically arranged in a tripod shape like "∴" around one of the screw holes (50) and the other three are symmetrically arranged in an inverted form like "∵" around the other screw hole (50). The protrusions are provided near the palate.

That is, when the screw is driven into the palate through one of the screw holes (50) formed at the front portion and the rear portion of the base member (10) to fix the palatal anchor plate to the palate, distal ends of the three cylindrical protrusions of the protrusion (30) first come into contact with the cortical bone in the palate, thereby preventing the base member (10) from compressing the palatal mucous membrane of a patient. Therefore, due to the cylindrical protrusions, the base member (10) does not press the palatal mucous membrane of a patient at all or just weakly comes into contact with the palatal mucous membrane when considering the average thickness of the soft tissue at the center of the palate. The palatal anchor plate enables ease of the procedure because there is no need for an incision of the palatal mucous membrane, thereby shortening the procedure time, improving patient convenience, and minimizing inflammation around the palatal anchor plate.

According to the embodiment, the three cylindrical protrusions constituting the protrusion (30) are arranged around the screw holes (50) so that the base member (10) is not deformed by excessive force when the screw is driven into the palate, thereby preventing the base member (10) from pressing the palatal mucous membrane of patients. The cylindrical protrusions of the protrusion (30) have a diameter of 1 mm and are spaced at a pitch (L) of 4 mm to minimize the contact area between the protrusion (30) and the palatal mucous membrane.

The height of the protrusion (30) is set to 1.0 to 1.2 mm by taking into consideration that the thickness of the soft tissue in the posterior part of the palate behind the palatal center (the position where the palatal anchor plate is actually fixed) is in a range of 1.0 to 1.2 mm on average. This setting is required because when the palatal anchor plate is fixed to a portion of the palate with the screws, the protrusion (30) first comes into contact with the cortical bone of the palate, thereby determining the position where the palatal anchor plate is fixed. Therefore, there is almost no compression of the tissue by the palatal anchor plate, thereby minimizing inflammation attributable to compression of the tissue and necrosis.

In addition, the hook portions (20) include the left portion and the right portion symmetrically extending from the left and right sides of the base member (10). In addition, engagement recesses (40) and (40') are formed in the posterior edge of the left portion and the right portion of the hook portion (20) at regular intervals. The engagement recesses (40) and (40') are formed to enable engagement with a traction member such as an orthodontic rubber band or a spring. The engagement recesses (40) and (40') are formed such that one or two engagement recesses (40') are provided at a horizontal portion and two to four engagement recesses (40) are provided at an inclined portion of each of the left portion and the right portion of the hook portion (20). That is, the hook portion (20) includes three to six engagement recesses (40) and (40'). The engagement recesses (40') provided at the horizontal portion of the hook portion are designed to enable easy movement of anterior teeth, and the engagement recesses (40) provided at the inclined portion of the hook portions are designed to enable easy application of intrusive and/or retractive forces to molars and premolars.

For example, as illustrated in FIG. 4, plates installed at left and right molars are connected to the engagement recesses (40) formed on the inclined portions of the posterior edge of the hook portion (20) via rubber band (power threads) so that traction forces are exerted on the left and right molars.

As illustrated in FIG. 3, predetermined screws (not denoted by reference symbol numbers) for fixing the screw holes (50) of the palatal anchor plate fixed through a gum (70) having a surface (60) to the cortical bone (80) and the cancellous bone (90) of a patient through the pair of the screw holes (50) by the screws. Here, the protrusion (30) is in contact with the palatal mucosa of a patient at three points, each contact point having a 1 mm diameter dot shape. Since the three protrusions are arranged in a tripod shape, the palatal anchor plate is stably positioned without being eccentrically loaded when they are fixed by the screws. Particularly, since the palatal mucosa of a patient is not pressed by the base member (10), there is no risk of necrosis of the underlying palatal mucosa.

Further, it is preferable that the hook portion (20) is integrally formed with the base member (10). With such structure, the palatal anchor plate is easy to adjust to the contour of an individual patient.

Therefore, ideally, the material of the palatal anchor plate has proper strength and properties enabling easy bending. According to the example, the palatal anchor plate is made of ASTM F67 pure titanium (Grade 3).

Although the present invention has been described in conjunction with exemplary embodiments illustrated in the accompanying drawings, the embodiments are disclosed only for illustrative purposes and should not be construed as limiting the present invention. On the contrary, those skilled in the art would appreciate that various modifications and equivalent embodiments are possible without departing from the spirit of the present invention. It is therefore to be understood that the true scope of protection of the present invention is defined by the following claims.

The invention claimed is:

1. A palatal anchor plate for orthodontic treatment, the palatal anchor plate comprising:
   a base member fixable to a palate by screws during orthodontic treatment of a tooth; and
   a hook portion comprising a left hook portion extending leftward from the base member and a right hook portion extending rightward from the base member, the left hook portion having a left horizontal portion and a left incline portion that is inclined relative to the left horizontal portion, the right hook portion having a right horizontal portion and a right incline portion that is inclined relative to the right horizontal portion,
   wherein, the base member has screw holes at a front portion and a rear portion thereof respectively, and around each of the screw holes, three tapered protrusions with round head are formed on a palatal side and arranged in a tripod shape, each tapered protrusion having a semi-spherical head,
   wherein engagement recesses are positioned a predetermined distance from each other and formed at a posterior edge of each of the left horizontal portion, the left incline portion, the right horizontal portion, and the right incline portion, thereby enabling engagement between the hook portion and a traction member, and
   wherein the palatal anchor plate is made of pure titanium ASTM F67 Grade 3.

2. The palatal anchor plate according to claim 1, wherein the hook portion has an inverted U shape.

3. The palatal anchor plate according to claim 2, wherein the protrusions have a height of 1.0 to 1.2 mm and a diameter of 1 mm.

4. The palatal anchor plate according to claim 3, wherein the engagement recesses include three to six engagement recesses on the hook portion.

5. The palatal anchor plate according to claim 1, wherein a distance between adjacent ones of the protrusions is 4 mm.

* * * * *